United States Patent [19]

Slemeyer

[11] Patent Number: 5,731,508
[45] Date of Patent: Mar. 24, 1998

[54] CALIBRATING GAS GENERATOR

[75] Inventor: Andreas Slemeyer, Marburg, Germany

[73] Assignee: Drägerwerk Aktiengesellschaft, Lübeck, Germany

[21] Appl. No.: 531,332

[22] Filed: Sep. 20, 1995

[30] Foreign Application Priority Data

Sep. 21, 1994 [DE] Germany ............... 44 33 607.1

[51] Int. Cl.[6] ............................................. G01N 31/00
[52] U.S. Cl. .................................. 73/1.03; 73/1.05; 436/9
[58] Field of Search ..................... 73/1 G, 1.03, 1.05; 436/9; 261/124

[56] References Cited

U.S. PATENT DOCUMENTS

| 3,943,774 | 3/1976 | Pollanz | 73/1 G |
| 4,069,701 | 1/1978 | Baldauf et al. | 73/1 G |
| 4,140,735 | 2/1979 | Schumacher | 73/1 G |
| 4,407,152 | 10/1983 | Guth | 73/1 G |
| 4,474,048 | 10/1984 | Schmidt | |
| 4,567,748 | 2/1986 | Klass et al. | 73/1 G |
| 5,493,891 | 2/1996 | Slemeyer | 73/1 G |

*Primary Examiner*—Hezron E. Williams
*Assistant Examiner*—Nashmiya Ashraf
*Attorney, Agent, or Firm*—Walter Ottesen

[57] ABSTRACT

The invention relates to a calibrating gas generator for generating a calibrating gas with a pregiven concentration of a calibrating gas component. The calibrating gas generator includes two vessels through which gas can flow. These two vessels contain the calibrating gas component in a calibrating solution and are connected in series. The temperature of the calibrating solution is controlled to a constant value by a temperature control apparatus. In order to improve the constancy of temperature, one of the vessels is arranged at least partially within the other vessel and this other vessel is configured, at least in part, as a heat insulating jacket for the one vessel.

21 Claims, 1 Drawing Sheet

CALIBRATING GAS GENERATOR

FIELD OF THE INVENTION

The invention relates to a calibrating gas generator for generating a calibrating gas with a pregiven concentration of a calibrating gas component.

BACKGROUND OF THE INVENTION

In order to calibrate gas analysis apparatus or gas sensors, test or calibrating gases are required. In the simplest case, gases contained in pressure cylinders are used. The use of these cylinders has the disadvantage that the concentration of the calibrating gas component is dependent upon the barometric pressure and therefore can be incorrect. Very low concentrations, for instance in the range of ppm, can only be produced within large limits of error and at high cost. For these reasons, the process of vaporizing of the calibrating gas component out of a solution at a defined temperature by means of a calibrating gas generator is preferred in these cases.

In order to perform the procedure, a calibrating solution containing the calibrating gas component in a certain concentration is brought into a thermostatic vessel, a so-called wash bottle. The evaporating solution is at equilibrium with the gas phase in which the desired concentration of the calibrating gas component correlating to the partial pressure occurs. A carrier gas, such as the ambient air, is passed through the solution by means of a pump so that the carrier gas is enriched with the calibrating gas component. A certain amount of the calibrating gas located above the solution and corresponding to the amount of the introduced carrier gas is discharged from the vessel.

In most cases the solvent is water. A known application for a calibrating gas generator is the calibration of breath-alcohol meters. In this case, the calibrating gas component is ethanol. The invention relates, without limitation to a particular solvent or a certain calibrating gas component, in general to calibrating gas generators for generating calibrating gas for the calibration of gas metering devices or gas sensors.

In order to improve the precision of the concentration of the calibrating gas component, especially in the case of a longer service life, it is a known procedure to introduce the gas discharged from the first wash bottle as a carrier gas to a second vessel connected downstream. Such a calibrating gas generator is known from U.S. Pat. No. 4,474,048. The gas discharged from the first vessel is, in turn, passed through the calibrating solution contained in the second vessel and is again discharged. By cascading the two vessels containing solutions, the through-flowing carrier gas is already in the first vessel almost completely enriched with the calibrating gas component. Only a small amount of the calibrating gas component is extracted from the second vessel in order to completely enrich the carrier gas with the calibrating substance until the desired partial pressure is reached.

In order to maintain the temperature and to thereby adjust the desired partial pressure, the vessels containing the calibrating solution are thermostatically monitored. Because the partial pressure is exponentially dependent upon the temperature, very high standards of precision are required with respect to the temperature measurement and the temperature control in order to achieve defined calibrating gas concentrations.

Calibrating gas generators of the kind mentioned above are, as a rule, operated with small through-flows since the required amounts of calibrating gas are mostly small. In this mode of operation, no large deviation from the equilibrium of temperature and concentration occurs. However, some gas metering devices and gas sensors require a high gas flow for monitoring and calibrating purposes. A high gas flow can lead to a disturbance of the thermal equilibrium and thus to a deviation of the calibrating gas concentration from the desired value.

Furthermore, the concentration in the calibrating gas becomes dependent upon the through flow rate and through flow amount which is not desired in many applications.

In breath-alcohol meters, for example, a high through flow of calibrating gas up to 30 l/min is needed. In a wash bottle with a calibrating solution volume of 0.5 liter, a temperature drop of about 1°/20° C. occurs in the calibrating solution when 5 liter of a carrier gas at a temperature 15° C. lower than that of the calibrating solution is passed through the latter /without vaporization heat being considered). Assuming the calibrating solution has a temperature of 34° C. and ethanol is the calibrating gas component, a reduction of over 0.3% of the ethanol concentration would result in the produced calibrating gas. This would be too high a reduction for most applications.

A further problem affecting the stability of temperature is caused by the effects of a low surrounding temperature on the temperature of the calibrating solution. One of these influences of temperature occurring in conventional calibrating gas generators occurs via the cover, which mostly consists of metal. This cover closes off the gas-filled space over the calibrating solution with respect to the ambient air. In the gas-filled space, the calibrating gas is withdrawn using a line and then diverted away upwardly. The heat transfer from the temperature-controlled calibrating solution to the cover occurs only via the gas. The foregoing parts of the vessel containing the calibrating solution which have contact with the calibrating solution only via the gas or which communicate with the calibrating solution via long paths in the material, are often much colder than the calibrating solution. Because of this, condensate can be produced which results in a change of the original concentration. The permeation of condensate into an apparatus can also lead to malfunctions.

A possible way to overcome this disadvantage would be to also heat the cover. This requires a complicated control mechanism and contains further sources of error. Another suggestion would be the use of a temperature-controlled wash bath in which all components of the calibrating gas generator are located. This requires a complex technical effort and, at the same time, restricts the transportability of the calibrating gas generator.

SUMMARY OF THE INVENTION

The object of the invention is to provide a calibrating gas generator for generating a calibrating gas having a pregiven concentration of a calibrating gas component so that the temperature stability of the calibrating gas generator and the calibrating solution is improved. In this way, the constancy of the concentration of the calibrating gas component is improved in the calibrating gas generated. The calibrating gas generator includes at least two vessels allowing the carrier gas to flow through them. The vessels are configured such that they can accommodate a calibrating solution containing the calibrating gas component and a gas-filled space located thereabove.

At least two of the vessels can be connected in series in such a manner that the carrier gas flows by means of a feed line through the calibrating solution, which can be filled into the first vessel, into the first gas-filled space located thereabove and back out of this first gas-filled space via a connecting line. By means of this connecting line, the carrier gas then flows through the calibrating solution, which is filled into the second vessel, into the second gas-filled space located thereabove. From here, the carrier gas can either be removed via a discharge line or transferred to another vessel. In order to regulate the temperature of the calibrating solution, at least one of the vessels is provided with a heating arrangement and a temperature measuring element.

The object of the invention, as described above, is realized according to one embodiment thereof wherein the second vessel of the at least two vessels is at least partially arranged within the first vessel. The first vessel is configured, at least in part, as a heat insulating housing for the second vessel. Advantageously, the arrangement is such that the second vessel is arranged inside the first vessel such that it is at least partially surrounded by the calibrating solution that can be filled into the first vessel and/or is at least partially surrounded by the gas-filled space of the first vessel.

By means of this embodiment of the invention, the influence of the ambient temperature on the calibrating solution contained in the second vessel is reduced substantially. The first vessel and the calibrating solution which can be filled into the first vessel or the gas-filled space above this calibrating solution serve as a protective layer for the second vessel. The influence of the ambient temperature on the top of the second vessel can also be reduced by arranging the top likewise inside the first vessel.

According to a further feature of the invention, which can also be reduced to practice independently from the embodiments described above, the at least two vessels are arranged atop a common base plate which has a high thermal conductivity or at least one of the two vessels is configured of a good heat conducting material. This measure affords the advantage that the temperature equalization is improved.

Another advantageous embodiment of the invention, which can be realized in combination with the embodiments mentioned previously or on its own, is configured such that at least one of the walls arranged above the gas-filled space in at least one of the two vessels is dome-shaped. This configuration causes that drops which have been formed by evaporation or which are tossed up from the calibrating solution and have accumulated on the wall of the vessel, can run down the wall and back into the calibrating solution.

An advantageous embodiment, which can be provided in combination with the other embodiments of the invention or on its own, is that the feed line, the connecting line, and/or the discharge line at least in part run along the inside of at least one of the vessels. Furthermore, it can advantageously be provided that the feed line, the connecting line, the discharge line, the line for filling a vessel with calibrating solution and/or the line used in order to drain a calibrating solution from a vessel, at least in part run along the inside of the base plate. The temperature stabilization and constancy are further improved by these features of the invention.

The advantages of the invention seen in relation to the state of the art are provided by the fact that the temperature of the calibrating gas generator remains constant, thereby improving the constance of the concentration of the calibrating component in the generated calibrating gas especially in the case of higher through-flow rates. The calibrating gas generator according to the invention is realized without a complex configuration.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
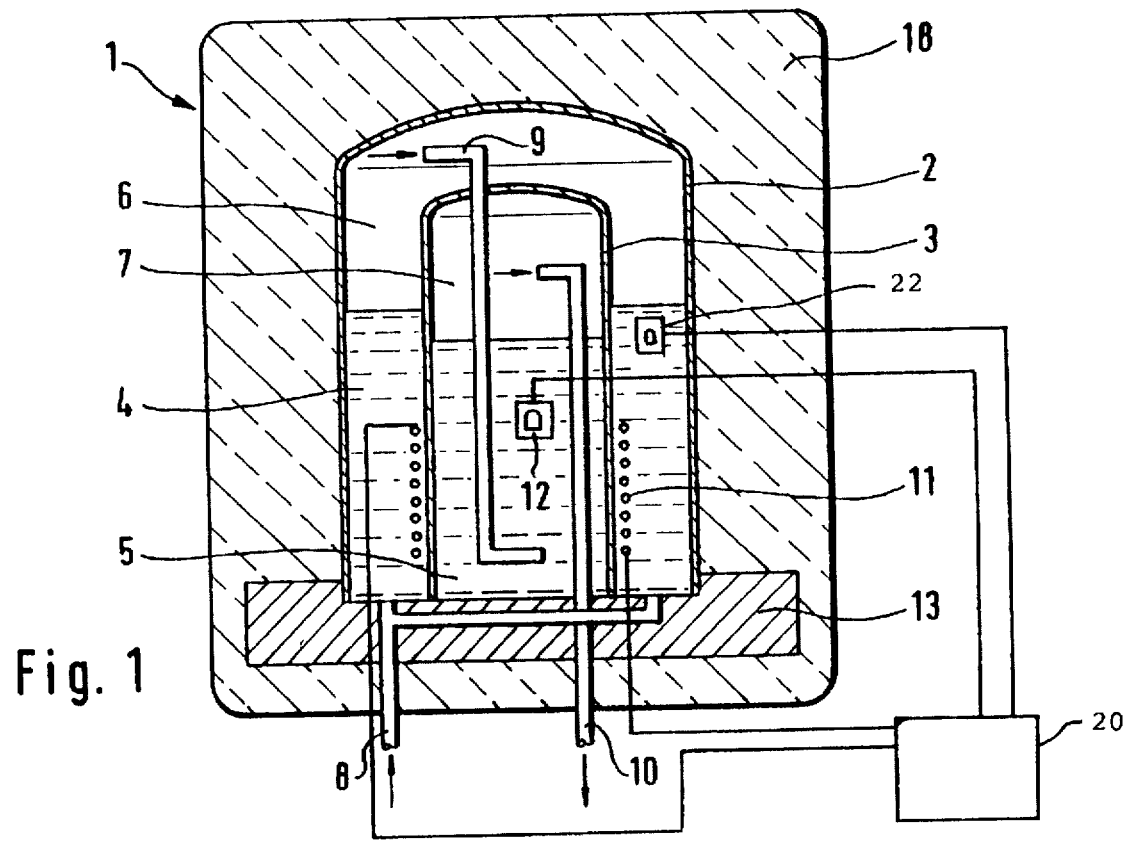
FIG. 1 shows a schematic cross section through a calibrating gas generator according to the invention; and, FIG. 2 shows another schematic cross section through a calibrating gas generator of FIG. 1.

The calibrating gas generator 1 in FIG. 1 includes two coaxially arranged, cylindrically-shaped vessels (2, 3). The second vessel 3 is arranged inside of the first vessel 2. Both vessels (2, 3) are partially filled with calibrating solution (4, 5) so that gas-filled spaces (6, 7) are above the calibrating solution in each of the vessels. The second vessel 3 is surrounded in part by the calibrating solution 4 in the vessel 2 and in part by the gas-filled space 6 above the calibrating solution 4 in the vessel 2. In this manner, the second vessel 3 is thermally insulated with respect to the ambient.

Figure 2:
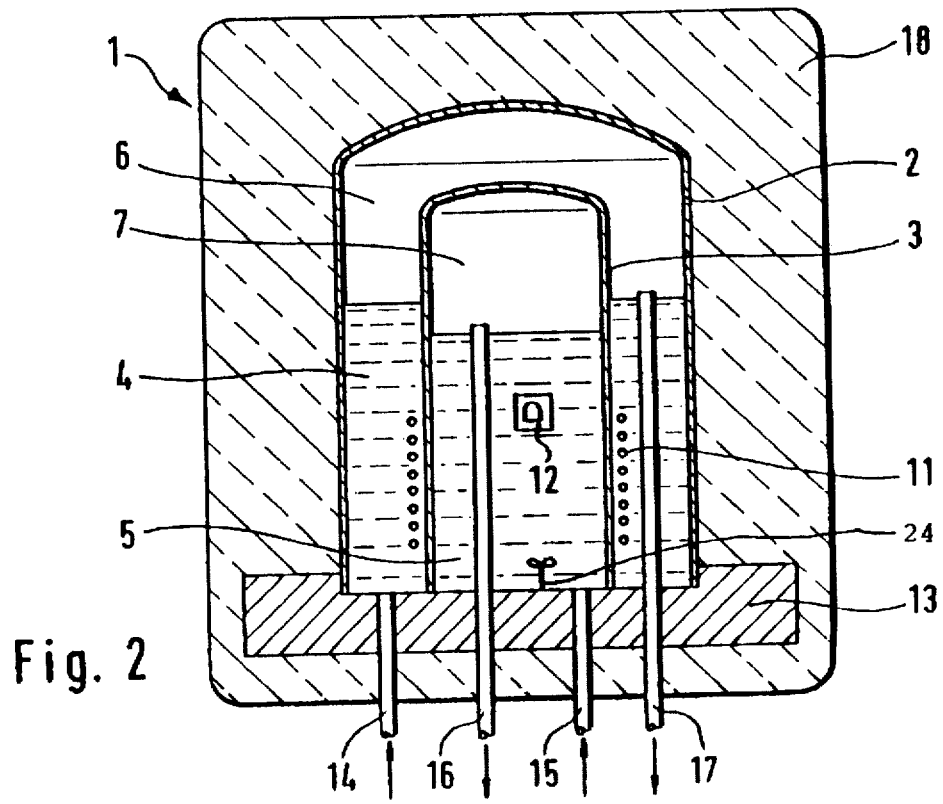

The two vessels (2, 3) have a dome-shaped upper wall so that drops of liquid which have accumulated there can run down the sides. The vessels (2, 3) are mounted on a massive metal base plate 13. The base plate contributes to the temperature equalization between the vessels (2, 3). The following all pass through the base plate 13: the supply lines for the gas flow, that is, the feed line 8 for carrier gas, the discharge line 10 for calibrating gas and, as shown in FIG. 2, the filling lines (14, 15) and the drain lines (16, 17) for the calibrating solution (4, 5) and the connecting lines for the heating arrangement 11 and the temperature measuring element 12. In this way, the supply lines also participate in temperature equalization.

The entire arrangement is surrounded by an insulating layer 18. This is especially advantageous when the vessels (2, 3) are made of a material that does not conduct heat well, such as glass or plastic, because the problem of a lower wall temperature above the calibrating solution level is especially high and the formation of condensate is improved. It is better to manufacture the vessels (2, 3) using a material with high thermal conductivity such as aluminum.

The carrier gas flow established by a pump (not shown) reaches the calibrating solution 4 in the first vessel 2 via the feed line 8. Here, the carrier gas flow is enriched with the calibrating gas component contained in the calibrating solution 4. The heating arrangement required in order to maintain the temperature at a constant level is preferably arranged inside the first vessel 2 so that the temperature losses occurring because of the carrier gas flow can be quickly compensated. The heating arrangement 11 is mounted on the wall facing toward the vessel 3 as shown. The material of this wall has high thermal conductivity thereby providing good heat transfer between the two vessels (2, 3).

The enriched gas displaced from the gas-filled space 6 reaches the second vessel 3 via a connecting line 9. This line 9 runs from the gas-filled space 6 above the calibrating solution 4 of the first vessel 2 into the calibrating solution 5 of the second vessel 3. In contrast to the calibrating gas generators previously known, no condensation can occur along this route, since the connecting line 9 is completely arranged within surroundings held at a constant temperature. In the calibrating solution 5 in the second vessel 3, the gas is enriched to its desired value with the calibrating gas component. The calibrating gas leaves the gas-filled space 7 above the calibrating solution 5 via the discharge line 10. A valve (not shown) in the discharge line 10 can be advantageously connected to the base plate 13 and can, in this way, be held at the same temperature.

The temperature measuring element 12 required for temperature control is arranged inside the second vessel 3. The temperature measuring element 12, along with the heating arrangement 11, is connected to the temperature control arrangement 20. The location in which the temperature measuring element 12 is arranged is advantageous because the temperature prevailing in the calibrating solution 5 of the second vessel 3 is the decisive variable.

The influence of the temperature in the ambient is reduced substantially by the arrangement of the invention of the vessels (2, 3) and the feed and discharge lines. The heat flow between the two vessels (2, 3) is determined by the temperature gradient therebetween. In the case of stationary equilibrium, that is, without the through flow of carrier gas, both vessels have the same temperature because of the close thermal coupling therebetween. The heat flow is equal to zero in this case. The heat losses occurring in the first vessel 2, due to gas flow, lead to brief heat losses in the second vessel 3 as well. By means of the control loop of the temperature control arrangement, the heating output of the heating arrangement 11 is increased in this case so that the temperature equilibrium is quickly restored. In this manner, it is possible to achieve a very precise control of temperature.

The minimal temperature drop of the calibrating solution 5 in the second vessel 3 due to gas flow occurring in the first vessel 2 can lead to the formation of condensate in the gas-filled space 7 of the second vessel 3. This disturbing formation of condensate can be prevented or reduced by adjusting the liquid level of the calibrating solution 4 in the first vessel 2 such that the second vessel 3 is completely covered. In this case, the top and sides of the gas-filled space 7 are surrounded by the calibrating solution 4 of the first vessel 2 and not by its gas-filled space. This results in a less dramatic temperature change affecting the second vessel 3, since the thermal capacity of the calibrating solution 4 is greater than that of the gas in the gas-filled space 6. Generally, the insulating effect of the first vessel 2 for the second vessel 3 is better the more calibrating solution 4 and the more gas-filled space 6 surrounds the second vessel 3. Thus, it can be advantageous for the reasons mentioned above if the portion of calibrating solution is greater than that of the gas-filled space 6.

If required, the first vessel 2 can contain a further temperature measuring element 22, which is also connected to the temperature control unit 20. The further temperature measuring element detects a temperature difference with respect to the desired value of temperature and this measured difference is used to control the heating output of the heating arrangement 11.

FIG. 2 shows how the supply connections for the supply of fresh calibrating solution (4, 5) can be provided with the aid of filling lines (14, 15) extending through bores in the base plate 13 and how the used solution can be removed by means of drainage lines (16, 17). It is advantageous in this case as well to lead all the lines through the base plate 13 since part of the temperature equalization can already take place here and thereby reduce the influence of the ambient on the calibrating solutions (4, 5).

The thermal conductivity of the material of the base plate 13 and/or at least one of the vessels (2, 3) is greater than 25 W/mK. This thermal conductivity is preferably greater than 100 W/mK and is especially preferably greater than 150 W/mK.

In order to increase the mixing of the calibrating solutions (4, 5) and thereby accelerate the temperature equalization, a mixing device 24 can be provided in one or both of the calibrating solutions. This mixing device is advantageously also built into the base plate 13 or can be magnetically driven.

It is understood that the foregoing description is that of the preferred embodiments of the invention and that various changes and modifications may be made thereto without departing from the spirit and scope of the invention as defined in the appended claims.

What is claimed is:

1. A calibrating gas generator for generating a calibrating gas having a pregiven concentration of a calibrating gas component, the calibrating gas generator comprising:

a first vessel having a vessel wall defining a first interior;

a second vessel having a vessel wall and defining a second interior and said second vessel being disposed at least partially in said first interior of said first vessel thereby permitting at least a portion of said first vessel to function as a heat insulating jacket for said second vessel;

feed means for supplying a calibrating solution containing the calibrating gas component to said first and second vessels so as to establish first and second liquid levels therein;

said first liquid level and at least a portion of the wall of said first vessel conjointly delimiting a first gas space above said first liquid level;

said second liquid level and a portion of the wall of said second vessel conjointly delimiting a second gas space above said second liquid level;

said vessel wall of said second vessel having a dome-like shape above said second gas space thereby permitting drops formed on said vessel wall of said second vessel above said second gas space to run down said vessel wall of said second vessel into the calibrating solution contained in said second vessel;

a first conduit for passing a carrier gas into the calibrating solution in said first vessel thereby allowing said carrier gas to become enriched with said calibrating gas component and reach said first gas space;

a second conduit for conducting the enriched carrier gas from said first space into the calibrating solution in said second vessel thereby allowing said carrier gas to become further enriched with said calibrating gas component and reach said second gas space;

a third conduit for conducting the enriched carrier gas away from said second gas space; and, temperature control means for controlling the temperatures of said calibrating solutions in said first and second vessels.

2. The calibrating gas generator of claim 1, said temperature control means comprising a heater element in one of said vessels and a temperature sensing device in the other one of said vessels; and, a control unit connected to said heater element and said temperature sensing device.

3. The calibrating gas generator of claim 2, said second vessel being mounted in said first vessel so as to cause the calibrating solution in said first vessel to at least partially surround said second vessel.

4. The calibrating gas generator of claim 3, said second vessel being mounted in said first vessel so as to cause the calibrating solution of said first vessel to cover said second vessel.

5. The calibrating gas generator of claim 1, said second vessel being mounted in said first vessel so that said second vessel is at least partially enclosed by said first gas space.

6. The calibrating gas generator of claim 1, further comprising a base plate made of a material having a high thermal conductivity; and, said first and second vessels being mounted on said base plate.

7. The calibrating gas generator of claim 6, wherein said base plate has a thermal conductivity greater than 25 W/mK.

8. The calibrating gas generator of claim 1, wherein at least one of said first and second vessels is made of good thermally conductive material.

9. The calibrating gas generator of claim 8, wherein said one vessel has a thermal conductivity greater than 25 W/mK.

10. The calibrating gas generator of claim 1, wherein the wall portion of said first vessel above said first gas space also has a dome-like shape.

11. The calibrating gas generator of claim 2, wherein said heater element is mounted in said first vessel and outside said second vessel.

12. The calibrating gas generator of claim 2, wherein said wall of said second vessel has an outer surface; and, said heater element is mounted next to said outer surface.

13. The calibrating gas generator of claim 2, wherein said temperature sensing device is mounted in said second interior.

14. The calibrating gas generator of claim 13, wherein said temperature control means includes a second temperature sensing device mounted in said first interior.

15. The calibrating gas generator of claim 1, at least one of said first, second and third conduits having a segment running in one of said first and second interiors.

16. The calibrating gas generator of claim 6, said feed means including a fill conduit for filling one of said vessels with said calibrating solution; and, said calibrating gas generator further comprising a drain conduit for draining said calibrating solution from said one of said vessels; and, at least one of said conduits having at least a segment in said base plate.

17. The calibrating gas generator of claim 1, mixer means for stirring the calibrating solution in at least one of said vessels for accelerating the equalization of temperature throughout said calibrating solution in said one of said vessels.

18. The calibrating gas generator of claim 17, said mixer means including a magnetic drive coupling.

19. The calibrating gas generator of claim 1, further comprising a heat insulating layer placed on said vessels.

20. The calibrating gas generator of claim 1, said vessel wall of said second vessel having an upper wall portion entirely within said first vessel; and, said first liquid level and at least a portion of the wall of said first vessel conjointly delimiting a first gas space above said first liquid level and above said upper wall portion of said second vessel.

21. A calibrating gas generator for generating a calibrating gas having a pregiven concentration of a calibrating gas component, the calibrating gas generator comprising:

a first vessel having a vessel wall defining a first interior;

a second vessel having a vessel wall and defining a second interior and said second vessel being disposed at least partially in said first interior of said first vessel thereby permitting at least a portion of said first vessel to function as a heat insulating jacket for said second vessel;

feed means for supplying a calibrating solution containing the calibrating gas component to said first and second vessels so as to establish first and second liquid levels therein;

said first liquid level and at least a portion of the wall of said first vessel conjointly delimiting a first gas space above said first liquid level;

said second liquid level and a portion of the wall of said second vessel conjointly delimiting a second gas space above said second liquid level;

said vessel wall of said second vessel having a dome-like shape above said second gas space thereby permitting drops formed on said vessel wall of said second vessel above said second gas space to run down said vessel wall of said second vessel into the calibrating solution contained in said second vessel;

a first conduit for passing a carrier gas into the calibrating solution in said first vessel thereby allowing said carrier gas to become enriched with said calibrating gas component and reach said first gas space;

a second conduit for conducting the enriched carrier gas from said first space into the calibrating solution in said second vessel thereby allowing said carrier gas to become further enriched with said calibrating gas component and reach said second gas space;

a third conduit for conducting the enriched carrier gas away from said second gas space;

temperature control means for controlling the temperatures of said calibrating solutions in said first and second vessels; and, said second vessel being mounted in said first vessel so as to cause the calibrating solution of said first vessel to cover said second vessel thereby reducing a formation of condensation in said second gas space above said second liquid level.

\* \* \* \* \*